(12) United States Patent
Mintchev

(10) Patent No.: US 9,707,392 B2
(45) Date of Patent: Jul. 18, 2017

(54) FEEDBACK CONTROLLED GASTRO-INTESTINAL STIMULATION

(75) Inventor: Martin P. Mintchev, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 521 days.

(21) Appl. No.: 12/681,775

(22) PCT Filed: Oct. 3, 2008

(86) PCT No.: PCT/CA2008/001751
§ 371 (c)(1),
(2), (4) Date: Apr. 5, 2010

(87) PCT Pub. No.: WO2009/043168
PCT Pub. Date: Apr. 9, 2009

(65) Prior Publication Data
US 2010/0222841 A1    Sep. 2, 2010

Related U.S. Application Data

(60) Provisional application No. 60/977,865, filed on Oct. 5, 2007.

(51) Int. Cl.
*A61N 1/36* (2006.01)
*A61B 5/053* (2006.01)
(Continued)

(52) U.S. Cl.
CPC .......... *A61N 1/36007* (2013.01); *A61B 5/053* (2013.01); *A61B 5/1107* (2013.01); *A61B 5/4238* (2013.01)

(58) Field of Classification Search
CPC ............ A61N 1/36085; A61N 1/36007; A61N 1/0509
(Continued)

(56) References Cited

U.S. PATENT DOCUMENTS 5,188,104 A   2/1993   Wernicke
5,540,730 A   7/1996   Terry, Jr.
(Continued)

FOREIGN PATENT DOCUMENTS

CN   1838978 A      9/2006
EP   1 641 522 A2   4/2006
WO   02/082968 A2   10/2002

OTHER PUBLICATIONS

Aelen, P., et al., "Feedback Control of Retrograde Peristalsis Using Neural Gastric Electrical Stimulation," Proceedings of the 30th Annual International Conference of the IEEE Engineering in Medicine and Biology Society, Vancouver, Canada, Aug. 20-24, 2008, 6 pages.

*Primary Examiner* — Alyssa M Alter
(74) *Attorney, Agent, or Firm* — Don D. Cha; Hamilton DeSanctis & Cha, LLP

(57) ABSTRACT

Neural Gastric Electrical Stimulation (NGES) is a new method for invoking gastric contractions under microprocessor control. However, optimization of this technique using feedback mechanisms to minimize power consumption and maximize effectiveness has been lacking. An apparatus and method are provided for inducing controlled gastro paresis. The apparatus comprises a contraction sensor, a stomach contraction generator, and a controller. The contraction sensor is responsive to circumferential contractions of the stomach, and outputs a signal indicative of a circumferential contraction. The stomach contraction generator induces a circumferential contraction upon receipt of an electrical signal from the controller. The controller sends the electrical signal to the generator upon receipt of the output signal from the sensor. The method comprises the steps of sensing a circumferential contraction of the stomach, and invoking a circumferential contraction of the stomach in response to sensing the circumferential contraction.

13 Claims, 10 Drawing Sheets

(51) Int. Cl.
*A61B 5/11* (2006.01)
*A61B 5/00* (2006.01)

(58) Field of Classification Search
USPC .......................................................... 607/40
See application file for complete search history.

(56) References Cited

U.S. PATENT DOCUMENTS

| | | | |
|---|---|---|---|
| 5,690,691 A * | 11/1997 | Chen et al. ..................... | 607/40 |
| 5,861,014 A | 1/1999 | Familoni | |
| 5,995,872 A | 11/1999 | Bourgeois | |
| 6,115,636 A | 9/2000 | Ryan | |
| 6,216,039 B1 | 4/2001 | Bourgeois | |
| 6,327,503 B1 | 12/2001 | Familoni | |
| 6,535,764 B2 | 3/2003 | Imran | |
| 6,600,953 B2 | 7/2003 | Flesler | |
| 6,826,428 B1 | 11/2004 | Chen | |
| 7,016,735 B2 | 3/2006 | Imran | |
| 7,054,690 B2 | 5/2006 | Imran | |
| 7,076,305 B2 | 7/2006 | Imran | |
| 7,146,216 B2 | 12/2006 | Bumm | |
| 7,502,649 B2 | 3/2009 | Ben-Haim | |
| 2003/0167025 A1* | 9/2003 | Imran et al. ..................... | 601/15 |
| 2004/0147816 A1 | 7/2004 | Policker | |
| 2005/0096514 A1 | 5/2005 | Starkebaum | |
| 2005/0096637 A1 | 5/2005 | Heruth | |
| 2005/0137643 A1* | 6/2005 | Mintchev ........................ | 607/40 |
| 2005/0149142 A1 | 7/2005 | Starkebaum | |
| 2005/0222638 A1 | 10/2005 | Foley | |
| 2006/0089699 A1 | 4/2006 | Imran | |
| 2007/0078494 A1* | 4/2007 | Mintchev ........................ | 607/40 |

* cited by examiner

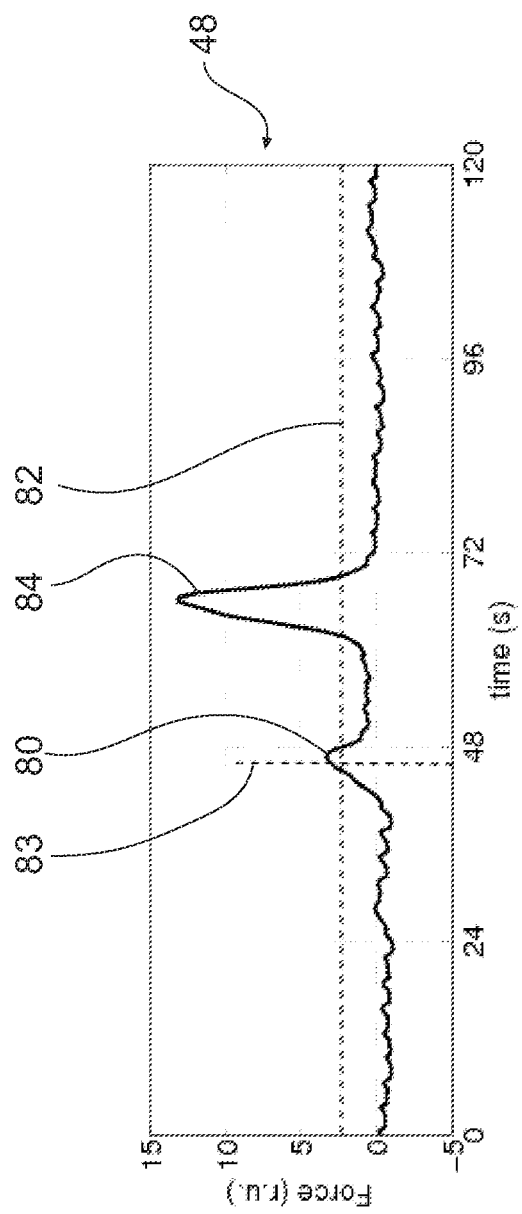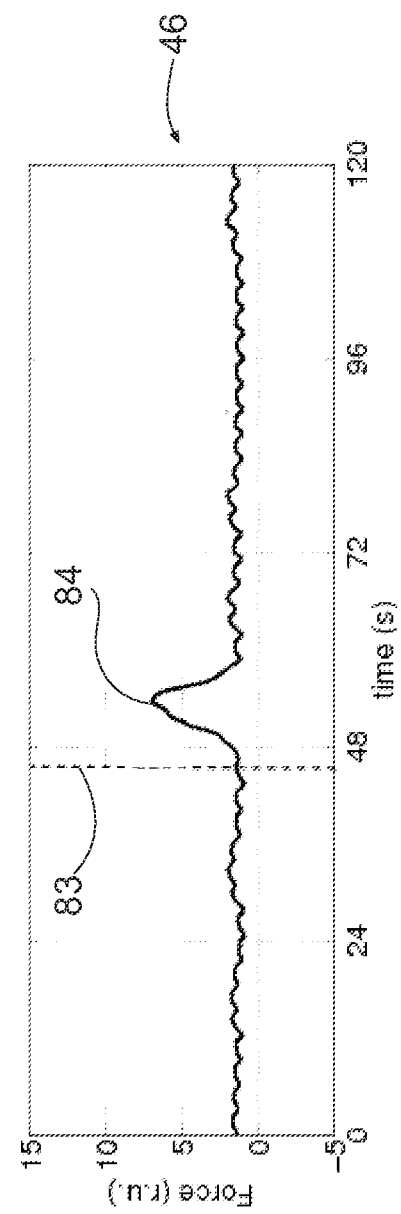
FIG. 6A
FIG. 6B

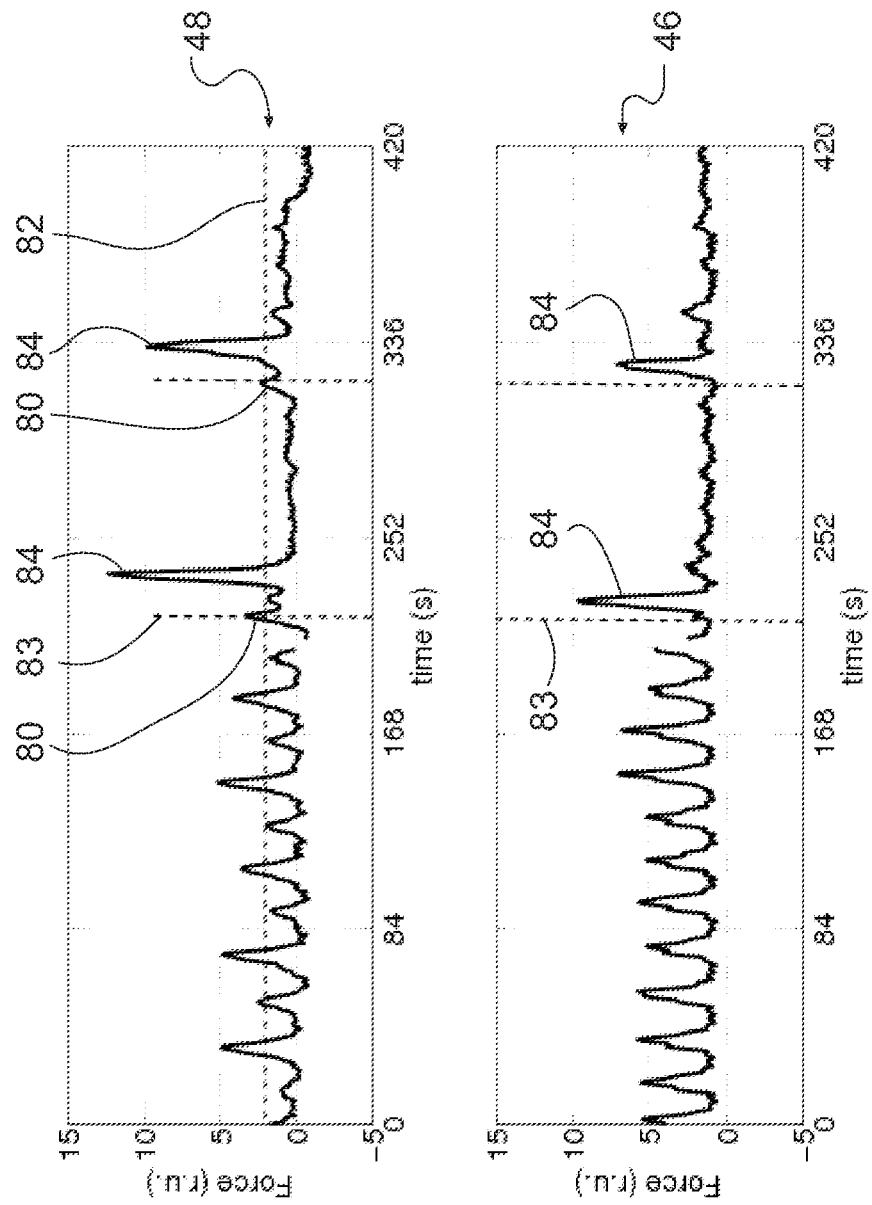

FEEDBACK CONTROLLED GASTRO-INTESTINAL STIMULATION

TECHNICAL FIELD

The apparatus and method relate to gastro-intestinal stimulation.

BACKGROUND

Feedback Controlled Gastric Electrical Stimulation (GES) has been used as a method of inducing symptoms of gastro paresis for the treatment of obesity. By producing retrograde peristalsis in the stomach, gastric emptying of the stomach can be delayed, leading to earlier feelings of satiety, a reduced appetite, and less food consumption. In US Patent Application Serial No. 20050149142 by Starkebaum, gastric stimulation is provided in a patient in response to sensed stomach activity.

There is a need for more efficient and less invasive ways of inducing symptoms of gastro paresis in a patient. There is also a need for the optimization of GES using feedback mechanisms to minimize power consumption and maximize effectiveness. The information disclosed in this document provides a unique apparatus and method that meets these needs.

SUMMARY

An apparatus is provided comprising a contraction sensor, a contraction generator, and a controller. The contraction sensor is located on a portion of the gastro-intestinal tract such as the stomach and is responsive to circumferential contractions of the portion of the gastro-intestinal tract. The contraction sensor has as output a signal indicative of a circumferential contraction of the portion of the gastro-intestinal tract. The contraction generator may for example be located closer to the pylorus than the contraction sensor. The contraction generator induces a circumferential contraction upon receipt of an electrical signal. The controller has, as at least one input, the output from the contraction sensor, and is configured to output an electrical signal to the contraction generator. The electrical signal is outputted upon receipt of output from the contraction sensor indicative of a contraction.

A method of controlled gastro paresis is provided, comprising the steps of sensing a circumferential contraction of a portion of the gastro-intestinal tract such as the stomach, and invoking a circumferential contraction of the portion of the gastro-intestinal tract in response to sensing the circumferential contraction. The sensed circumferential contraction is sensed at a first location on the portion of the gastro-intestinal tract. The invoked circumferential contraction is invoked at a second location on the portion of the gastro-intestinal tract. In the case of the portion of the gastro-intestinal tract being the stomach, the second location may be located closer to the pylorus than the first location.

BRIEF DESCRIPTION OF THE FIGURES

Embodiments will now be described with reference to the figures, in which like reference characters denote like elements, by way of example, and in which:

FIGS. 6A and 6B are graphs created with data from force transducers used as part of a feedback controlled gastric stimulator;

FIGS. 7A and 7B are graphs that show signs of induced gastro paresis, the graphs created with data from force transducers used as part of a feedback controlled gastric stimulator;

DETAILED DESCRIPTION

Neural Gastric Electric Stimulation (NGES) is a type of GES that generates multi-channel high energy, high frequency waveforms that can directly invoke contractions which can move gastric content in a controlled fashion depending on the synchronization between the stimulating channels. NGES overrides any spontaneously-existing electromechanical events and does not entrain the intrinsic gastric slow waves. By stimulating the local network of cholinergic neurotransmitters, repeated local contractions can be produced. This stimulation technique has been successful in accelerating gastric emptying of both liquids and solids and in producing strong, externally-controlled, retrograde contractions.

Obesity and Gastric Motility

The possibility to produce retrograde contractions in the stomach using GES is of particular interest for the treatment of obesity, which is considered as one of the most pressing health problems of modern society. The prevalence of obesity has increased significantly in the period of 1988-1994 and is still growing. Various disorders and conditions have been related to obesity, many of which are life-threatening. GES is a promising technique to treat obesity that could provide reliable long term results without suffering from the side effects associated with pharmacotherapy or from the postoperative complications related to bariatric surgery. Invoked and appropriately controlled retrograde peristalsis could be an important avenue for delaying gastric emptying and thus indirectly controlling satiety and food intake. Since NGES is the only method that can invoke retrograde contractions, it could be regarded as the GES method of choice for the treatment of obesity. However, this technique is energy-demanding, and if utilized in an open-loop setup could pose difficult, if not impossible long-term requirements for a multi-channel programmable implant. Moreover, recent chronic studies on experimental animals indicated that although the method was effective in reducing food intake, frequently invoked contractions in an open-loop system may lead to tissue accommodation resulting in NGES losing its ability to invoke contractility using the same amplitude of the stimulating voltage. Therefore, optimization of the invoked contractile patterns using feedback control is an important avenue to increase the effectiveness and the applicability of NGES.

Figure 1:
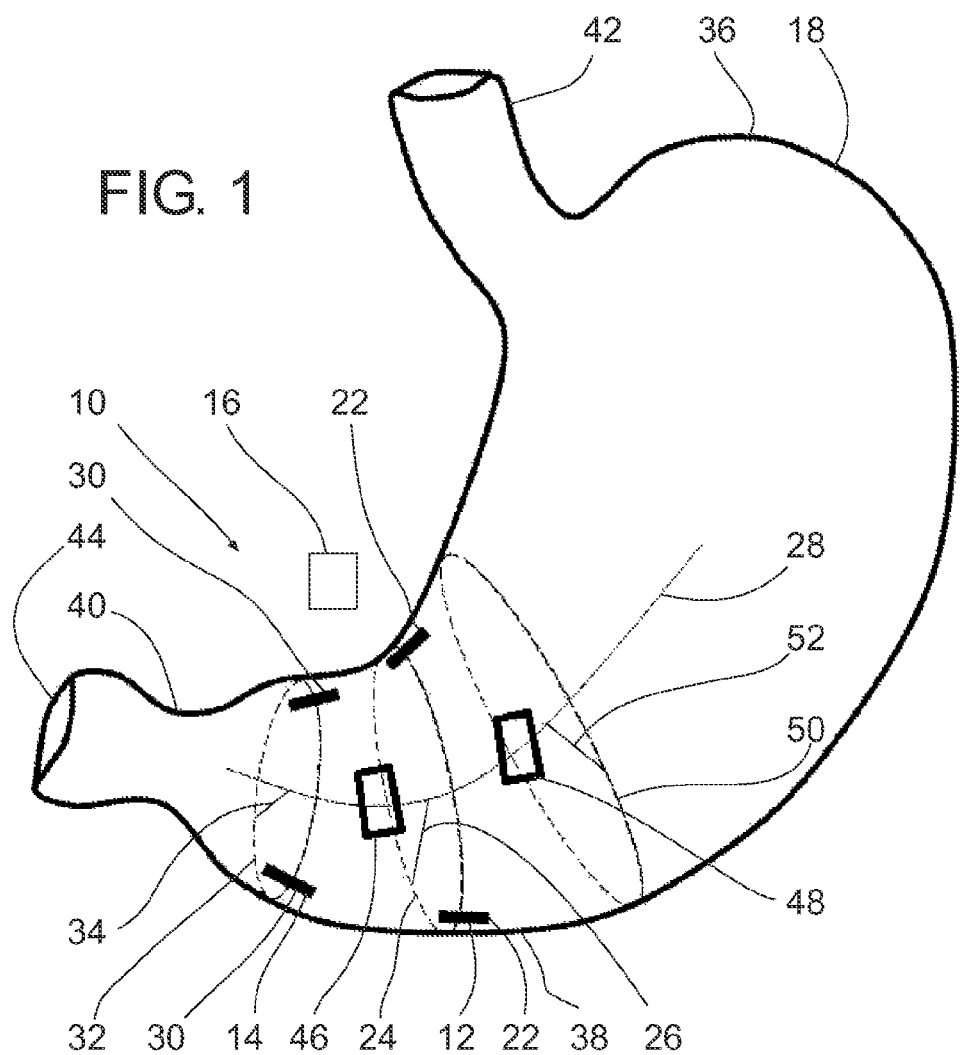
FIG. 1 is side elevation view, partially in section, of a feedback controlled gastric stimulator positioned in the stomach.

Referring to FIG. 1, a feedback controlled gastric stimulator 10 is illustrated comprising a contraction sensor 12, a stomach contraction generator 14, and a controller 16. Contraction sensor 12 is located on a stomach 18 and is responsive to a circumferential contraction of stomach 18. Contraction sensor 12 has as output a signal indicative of a circumferential contraction of the stomach. Stomach 18 has a gastric axis 28, a fundus 36, an antrum 38, and a pylorus 40. Gastric axis 28 defines the center of an infinite number of imaginary circumferences of stomach 18 running from an esophagus 42 to a duodenum 44. Stomach contraction generator 14 is located on stomach 18 closer to pylorus 40 than contraction sensor 12. Contraction generator 14 is located to induce a circumferential contraction upon receipt of an electrical signal arriving at contraction generator 14. Controller 16 has at least one input from contraction sensor 12 and is configured to output the electrical signal to contraction generator 14 upon receipt of output from contraction sensor indicative of a circumferential contraction.

Contraction sensor 12 comprises a first set of electrodes 22 implanted in stomach 18. First set of electrodes 22 are implanted circumferentially around a first circumference 24 defined by a radius 26 about gastric axis 28 in stomach 18. First set of electrodes 22 may comprise any number of electrodes, although a number greater than one is preferred. Electrodes of first set of electrodes 22 may be positioned transverse one another in order to afford maximum sensitivity to a circumferential contraction. If two electrodes are employed, this means that the electrodes are spaced diametrically around first circumference 24. Contraction generator 14 comprises a second set of electrodes 30 implanted in stomach 18. Second set of electrodes 30 are implanted circumferentially around a second circumference 32 defined by a radius 34 about gastric axis 28. Second set of electrodes 30 may comprise any number of electrodes, although a number greater than one is preferred. Electrodes of second set of electrodes 30 may be positioned transverse one another in order to afford maximum efficiency in invoking a circumferential contraction. If two electrodes are employed, this means that the electrodes are spaced diametrically around second circumference 32. Sets of electrodes 22 and 30 are provided as sets of stainless steel electrodes (commonly available such as Temporary Cardiac Pacing Wire, Weck Cardiac Pacing Wires, Research Triangle Park, N.C., USA). Sets of electrodes 22 and 30 may be subserosally implanted at both sides of the anterior wall of antrum 38 of stomach 18 during laparotomy. Alternatively, gastric stimulator 10 may be implanted without surgical techniques. Each set of electrodes 22 and 30 comprises 1-cm active and reference electrodes. A second set of electrodes 30 may for example be positioned two—three cm proximal to pylorus 40, with first set of electrodes 22 positioned three—four cm proximal second set of electrodes 30. Controller 16 is configured to apply to second set of electrodes 30 an electrical current that overrides natural contractions of stomach 18. Controller 16 may also be configured to apply the electrical current to first set of electrodes 22 as well.

Figure 2:
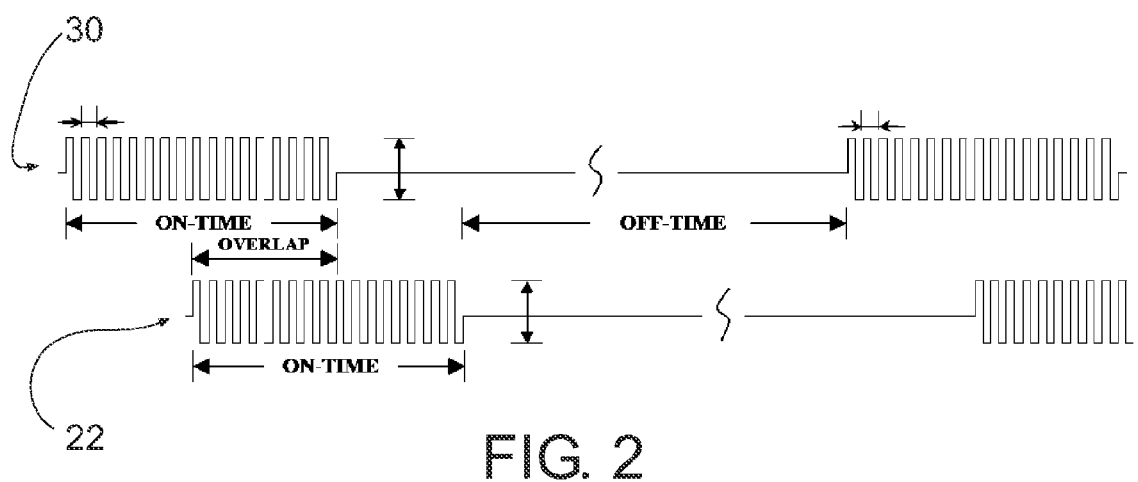
FIG. 2 shows a retrograde stimulation pattern.

Controller 16 may be a custom-designed external neurostimulator. Controller 16 may include custom-designed hardware and software modules developed to implement a two-channel feedback-controlled neural gastric electrical stimulator. The controlling software may be designed using software such as Labview (National Instruments, Austin, Tex., USA). Both sets of electrodes 22 and 30 may be employed in applying electrical currents to stomach 18. Referring to FIG. 2, controller 16 generates two-channel, controlled, charge-balanced bipolar rectangular voltage waveforms at a frequency of 50 Hz with an adjustable amplitude, duty cycle, on- and off-time and overlap between channels. By sequentially activating the channels (each channel corresponding to one of sets of electrodes 22 and 30), the direction of propagation of an invoked circumferential contraction can be controlled. Preferentially, second set of electrodes 30 are activated first, in order to initiate retrograde circumferential contractions that prevent food from being peristaltically emptied from stomach 18. Controller 16 is implemented in software and the synthesized digital waveforms may be converted to voltages by a digital to analog converter such as a DAQCard-AI-16XE-50 (National Instruments, Austin, Tex., USA). A simple analog buffer amplifier provides the necessary current.

Referring to FIG. 1, controller 16 may be configured to sense a natural circumferential contraction of stomach 18 in a number of ways. Controller 16 may be configured to measure impedance between electrodes of first set of electrodes 22. In this case, first set of electrodes 22 may not only measure the impedance between electrodes but may also apply stimulation in concert with second set of electrodes 30. Alternatively, gastric stimulator 10 may include a set of force transducers 46 and 48. Force transducers 46 and 48 may be implanted on the anterior gastric wall along gastric axis 28, three and a half to four cm apart. Force transducers 46 and 48 are located at different points on the inside of stomach 18. As shown in FIG. 1, force transducer 46 is located at a point on first circumference 24, while force transducer 48 is located on a third circumference 50 defined by a radius 52 about gastric axis 28 in stomach 18. Alternatively, force transducers 46 and 48 may be located along any other circumference of stomach 18, provided that force transducer 46 is located proximal second circumference 32, and force transducer 48 is located proximal force transducer 46. Force transducers 46 and 48 measure the force of deformation of the stomach wall in order to detect a circumferential contraction. Force transducers 46 and 48 may be strain gauge transducers, examples of which can be purchased from RB Products (Stillwater, Minn., USA). Recordings from transducers 46 and 48 may be acquired using a custom-designed analog bridge amplifier with frequency bandwidth between 0 and 1 Hz and digitized using a 10-Hz sampling frequency, and may be acquired by custom-designed software. The strength of gastric contractions, which is a measure of the spontaneous propulsive gastric motility, is assessed directly with the proximal force transducer, and indirectly with the interelectrode impedance of the proximal implanted channel.

NGES for the treatment of obesity is based on the idea of overriding spontaneously existing slow waves by invoking local retrograde contractions to delay gastric emptying.

However, spontaneously-existing propulsive gastric motility is a rather infrequent process, only active in the period after a meal and in some of the four phases of the migrating motor complex. Therefore, a feedback mechanism for NGES control is very beneficial for retrieving the timing of the spontaneously-existing contractile activity and adjusting the NGES timing accordingly.

Bioimpedance has been routinely quantified as:

$$=z \; L/A \quad [1]$$

where Z is the electrical impedance of the tissue [Ω] having both a resistive and a reactive (capacitive) component, Z is its specific impedance [Ω cm], L is the distance between the centers of the measuring electrodes [cm], and A is the tissue cross sectional area [cm$^2$].

Figure 4:
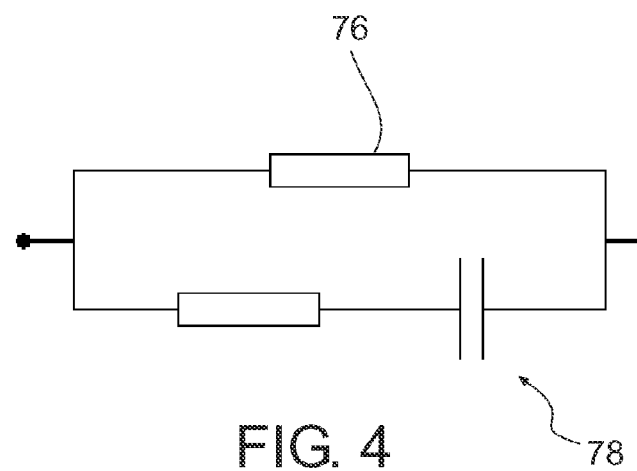
FIG. 4 shows a theoretical model of tissue impedance.

When electrical tissue properties are relatively constant over time, it is possible to estimate volumes encompassed by transversely positioned electrodes. Because antral contractions decrease the cross-sectional area at the location of a contraction and due to the specific electrode implantation technique that used, interelectrode impedance can be a measure of contraction strength in the vicinity of a given transversely-implanted electrode pair. In general, the tissue impedance between a transversely-implanted electrode pair is frequency dependent, and this is manifested by the presence of a capacitive component. Referring to FIG. 4, a model that is commonly used in the literature comprises a resistor 76 in parallel with a non-ideal capacitor 78. The resistive component represents the conductive characteristics of the extracellular body fluid, while the reactive component has its complex origin in the cellular membranes which act as leaky, non-ideal capacitors. When measuring the impedance, an interrogating low-frequency current cannot pass through the cellular membranes and can only flow through the extracellular fluid. Alternatively, an interrogating high-frequency current can pass the cellular membranes resulting in a combined intra- and extracellular conductive pathways. The impedance of smooth muscle tissue is in the range of $10^2$ to $10^3$ Ω cm for frequencies between 100 Hz and 10 MHz. Referring to FIG. 1, with the transversally-implanted electrodes first set of electrodes 22 located for example four to five cm apart, the inter-electrode impedance as a measure for the contractile strength at their vicinity can then be used in the feedback loop. The frequency may be selected so that the difference between no contraction and maximum contraction is the highest. This frequency may be determined experimentally in the case of the electrode configuration shown. By using an impedance measurement system that is frequency-adjustable, with a minimum of about 5 kHz, influence of other bioelectric signals like ECG, EEG and EMG may be avoided and likewise stimulation of muscles and nerves may be avoided. Frequency maximum in this case is about 500 kHz, limited by the parasitic capacitances between the electrode leads as well as these between the ground and the measured object.

The impedance measurement device may include a voltage controlled oscillator (VCO) to control the oscillation frequency. The output voltage of this VCO may be applied to the gastric tissue via first set of electrodes 22 when NGES is not taking place. The current through the tissue may be measured and converted into voltage by a transimpedance amplifier.

a. Voltage Controlled Oscillator (VCO)

In the present design an integrated circuit such as MAX038 (Maxim Integrated Products Inc., Sunnyvale, Calif., USA) may be used for the VCO. If the integrated circuit is a current-controlled oscillator whose frequency depends on the provided current and on an external capacitor, oscillation bandwidth may be controlled by selection of the capacitor, for example by using a quad digital switch such as a MAX4679 (Maxim Integrated Products Inc., Sunnyvale, Calif., USA). The output voltage delivered by the oscillator may be 2 Vpp constant over the entire frequency range.

Along with the sinusoidal output, the VCO may be selected to provide a synchronous and a 90-degrees out of phase quadrature square wave output. If these outputs are not of the same magnitude and have a DC offset, a highpass filter and a comparator (such as a MAX903 (Maxim Integrated Products Inc., Sunnyvale, Calif., USA) may be used to convert the synchronous and quadrature waves to equal amplitude outputs. The signals may be high-pass filtered if the comparator has an output offset.

Transimpedance Amplifier

In the embodiment shown, the current through the tissue flows to the virtual ground of a transimpedance amplifier and is converted to a voltage by a resistor connecting the inverting input to the output of the amplifier.

a. Synchronous Demodulation

Current flow through the time-dependent inter-electrode impedance can be regarded as an amplitude modulated (AM) signal. By demodulating the signal, the amplitude and the phase of the inter-electrode impedance may be retrieved. Assuming that the voltage across the tissue is:

$$(t)=V \cos 2\pi f_c t \quad [2]$$

where V is the stimulation voltage amplitude [V], $f_c$ is the frequency of the stimulating signal [Hz] and t is time [s], the current through the tissue is then given by:

$$(t)=I(t)\cos 2\pi f_c t+\phi(t)=I(t)\cos \phi(t)\cos 2\pi f_c t-I(t)\sin \phi(t)\sin 2\pi f_c t \quad [3]$$

Figure 5:
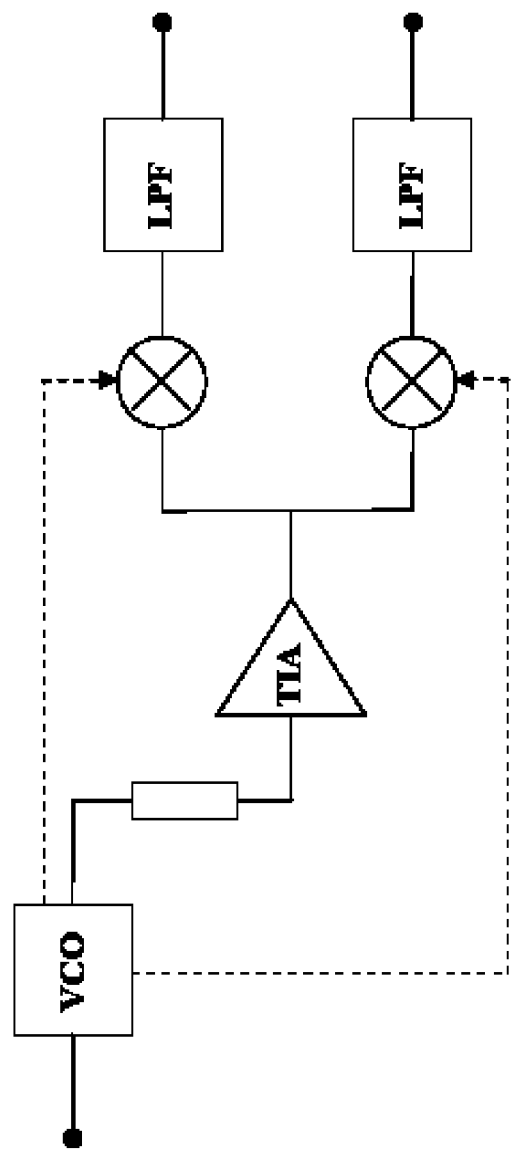
FIG. 5 shows a circuit diagram for the synchronous demodulation of the current used with the gastric stimulator of FIG. 1.

Referring to FIG. 5, synchronous demodulation may be performed by multiplying the retrieved signal by the synchronous and the 90-degrees de-phased signal and then low pass filtering the result. The low pass filters may be simple first-order RC filters, and may be employed to filter out any parasitic signal component with doubled frequency introduced by the multiplying operation.

After introducing:

$$R(t)=(V/(I(t)\cos \phi(t)))^{-1} \text{ and } X(t)=(V/(I(t)\sin \phi(t)))^{-1}, \quad [4]$$

so that V*R(t) and V*X(t) are the in-phase and the quadrature components of i(t), the measured impedance is Z(t)=V/i(t), where R(t) and X(t) are the resistive and the reactive components of Z(t), respectively.

Figure 11:
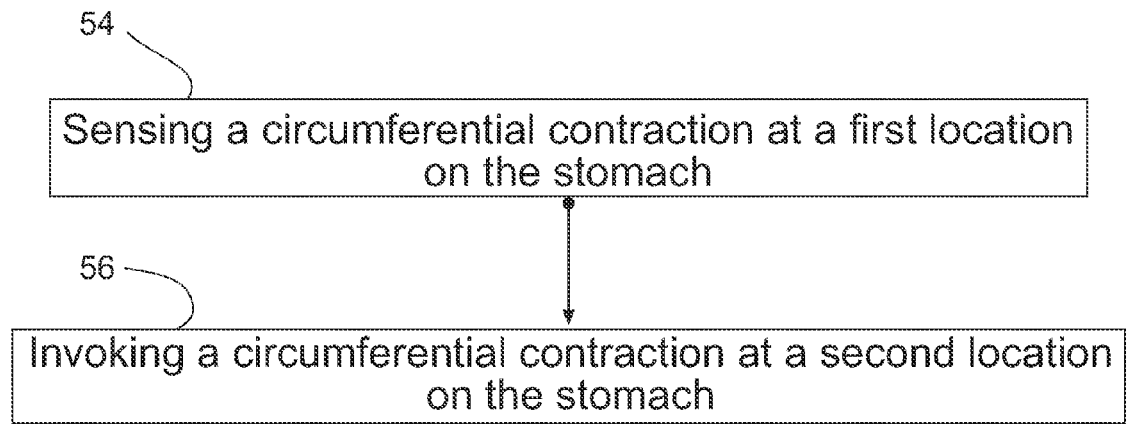
FIG. 11 shows a method of sensing a circumferential contraction and invoking a retrograde contraction.

Referring to FIG. 11, a method of inducing controlled gastro paresis is illustrated. In step 54, a circumferential contraction of stomach 18 is sensed at a first location on stomach 18. The first location corresponds to first circumference 24 where first set of electrodes 22 are located. Step 54 may involve sensing a circumferential contraction by measuring the impedance between first set of electrodes 22 implanted in stomach 18. Alternatively, step 54 may involve sensing a circumferential contraction by measuring the force of deformation of the wall of stomach 18. In step 56, a circumferential contraction is invoked in response to the sensed circumferential contraction of step 54. The invoked circumferential contraction is invoked at a second location on stomach 18 closer to pylorus 40 than the first location. Second location corresponds to second circumference 32 where second set of electrodes 30 are located. The contraction is invoked in the antrum of the stomach. In step 56, invoking a contraction comprises applying an electrical current to stomach 18 at second circumference 32. In addition, an electrical current may be applied to stomach 28 at a third location, the third location being further from pylorus 40 than the second location. The third location may correspond to first circumference 24, and the electrical current may be applied by first set of electrodes 22. Alternatively, the third location may correspond to a different location, and may be applied using an additional electrode set-up. The invoked contraction overrides the naturally occurring circumferential contraction sensed at first circumference 24.

Figures 10A, 10B, 10C:
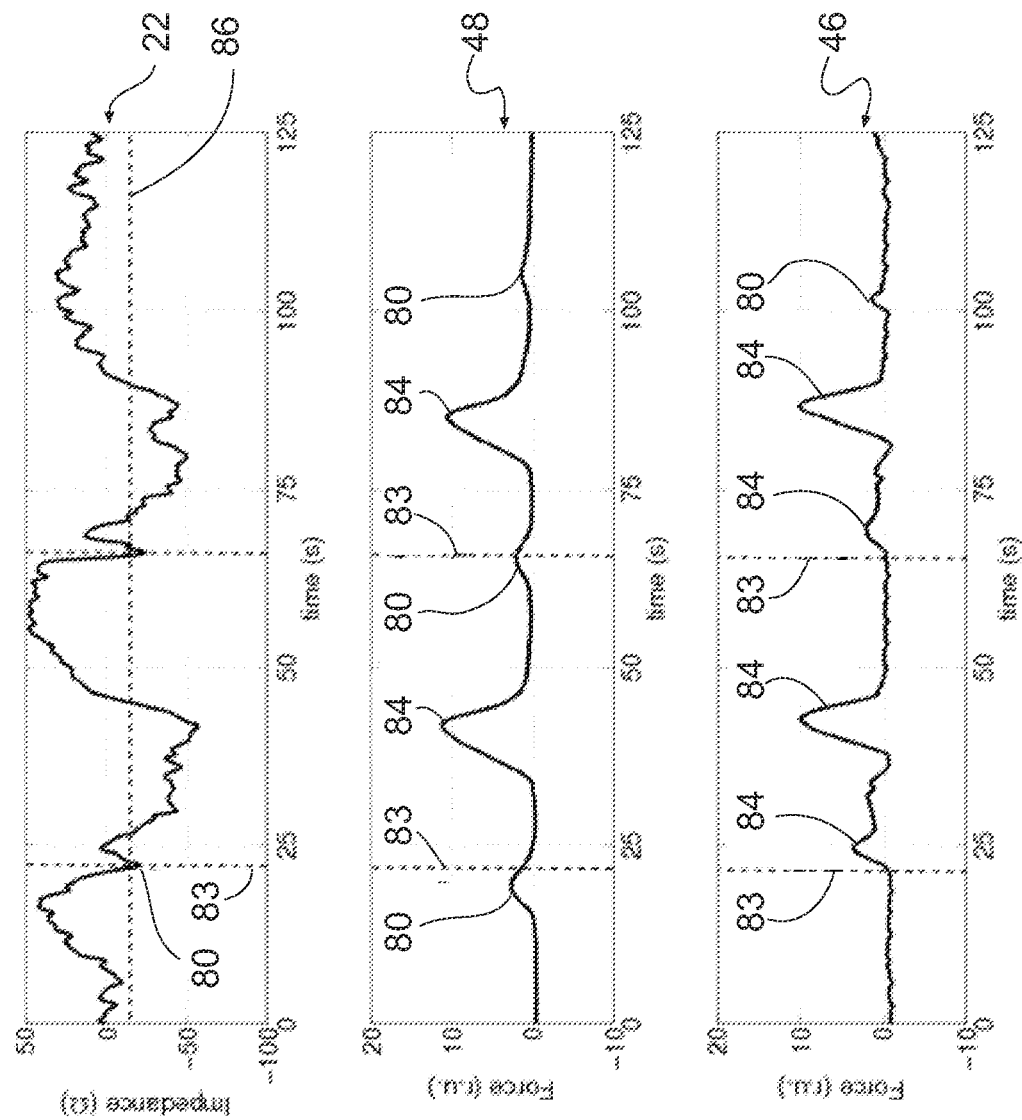
FIGS. 10A-10C are graphs that show signs of induced gastro paresis, the graphs showing correlation between the force transducers and the impedance sensor in a feedback controlled gastric stimulator.
Figure 13:
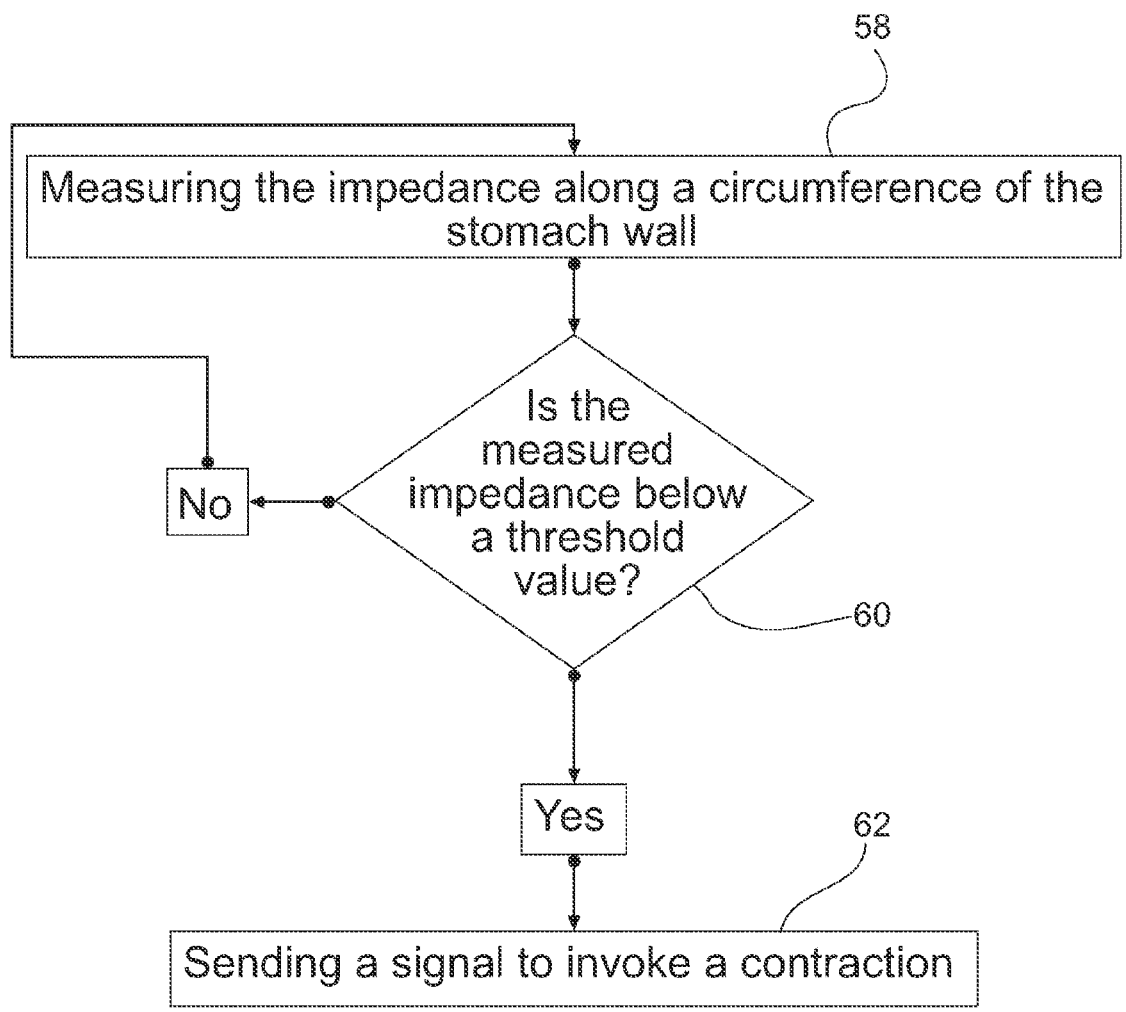
FIG. 13 shows a method of detecting a circumferential contraction using the impedance along a circumference of the stomach wall.

Referring to FIG. 13, a method for sensing a circumferential contraction using the impedance of the wall of stomach 18 is illustrated. In step 58, the impedance is measured along a circumference of the wall of stomach 18. This may be accomplished as described above using first set of electrodes 22. In step 60, the measured impedance is compared to a threshold value. Since impedance will decrease during a circumferential contraction, if the measured impedance is above the threshold value, than the method returns to step 58 and re-measures the impedance. This process is repeated, until a measured impedance value is returned that is below the threshold value. Referring to FIG. 10A, because impedance measurements tend to drift over time, it may be necessary to process the measured impedance prior to comparing it to the threshold value. This processing may involve subtracting a moving average from the measured impedance, in order to compensate for drift variations in the measured impedance. The moving average may be calculated using the past twenty seconds of measured impedance values. Alternatively, other ranges of time of measured impedance values may be used to calculate the moving average. Additionally, a different processing method other than subtracting a moving average may be employed, such as higher-end statistical calculations. Referring to FIG. 13, once a circumferential contraction has been sensed, as indicated by a processed measured impedance value below the threshold value, a signal is sent to invoke a contraction in step 62.

Figure 8:
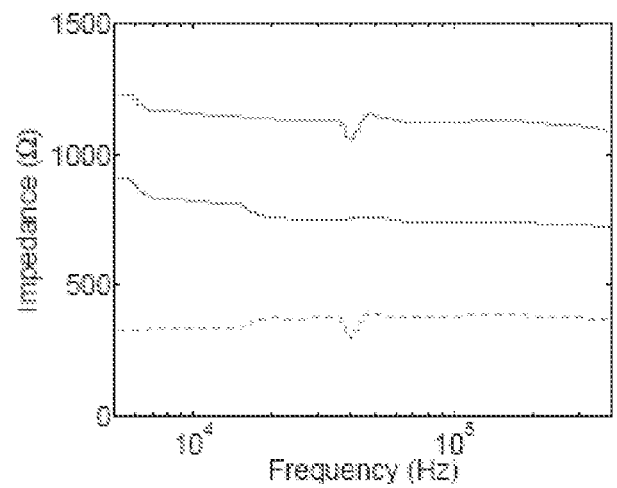
FIG. 8 is a graph that shows a search for the optimal impedance interrogation frequency.

An embodiment of the impedance measurement device was tested on a piece of beef tripe (not shown) to find the optimal interrogation frequency. Two electrodes were placed on the tripe 5 cm apart and a frequency sweep from 5 kHz to 500 kHz was performed. After the first sweep the tripe was pulled together so that the inter-electrode distance was reduced to 2.5 cm. Another frequency sweep was performed to find the impedance in this contracted state. Referring to FIG. 8, the results from both sweeps are depicted. The change from extracellular to intracellular conduction was estimated at the relatively low frequency of 6 kHz. There was no change in the phase of the impedance. The inter-electrode impedance difference between contracted and uncontracted states was approximately 350 Ω for all frequencies, indicating there was no favorable frequency. The small deflection at 35 kHz was caused by switching of the VCO capacitors at that frequency. Finally, a frequency of 50 kHz was chosen, which is considered a preferred frequency for single frequency bioimpedance measurements.

Figure 9A:
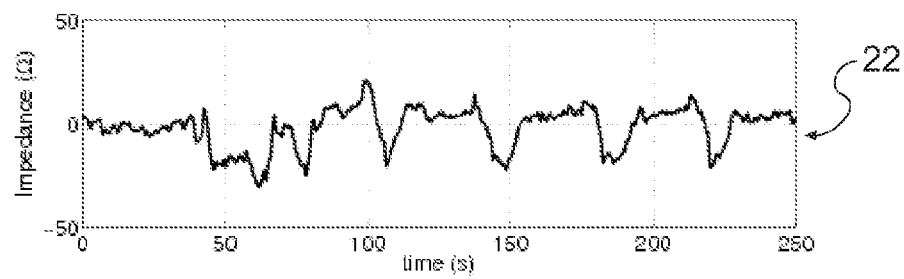
FIGS. 9A-9C are graphs that show the correlation between the force transducers and the impedance sensor in a feedback controlled gastric stimulator.
Figure 9B:
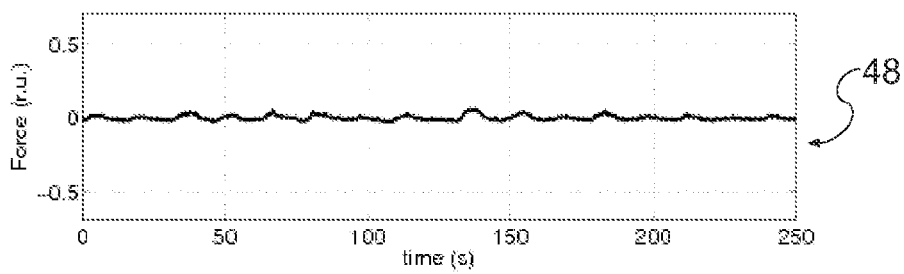
Figure 9C:
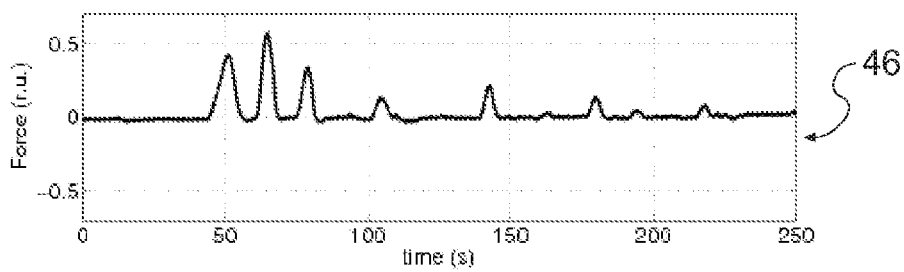

Referring to FIG. 8, the baseline impedance value drifted over time. To compensate for this phenomenon a 20-second moving average was calculated and subtracted from the actual impedance. Referring to FIGS. 9A-9C, the adjusted impedance values for first set of electrodes 22 showed good correlation with the force measurements of force transducers 46 and 48 ($r=0.6$, $p<0.001$). The deviations resulting from natural and NGES-induced contractions are in the 100-Ω order of magnitude. Referring to FIGS. 10A-10C the results gastric stimulator 10 using an inter-electrode impedance-based feedback system are shown. Measurements for force transducers 46 and 48 are included only to provide proper illustration, and need not be employed with gastric stimulator 10. A trigger level 86 for the impedance measurements was reversed, since the inter-electrode impedance decreases during natural contraction 80. Similarly to the results with force-based feedback, invoked contractions 84 triggered by the impedance feedback were higher in amplitude then natural contractions 80. Invoked gastro paresis was also observed after the inter-electrode impedance-based feedback was activated.

The method illustrated in FIG. 13 may also be used to sense a circumferential contraction anywhere in the gastrointestinal tract, substituting pylorus 40 with the rectum (not shown) of the patient, and stomach with the gastrointestinal tract. In this case, a contraction may be invoked along a second circumference (not shown) of the gastrointestinal tract, as defined by a radius (not shown) of gastric axis 28, the second circumference being closer to a rectum (not shown) than the first circumference (not shown). A contraction may be invoked, as before, by applying an electrical current to the gastrointestinal tract along the second circumference. Additionally, an electrical current may also be applied to the gastrointestinal tract along either the first circumference, or along a third circumference (not shown) defined by a radius (not shown) of the gastrointestinal tract. If the electrical current is also applied along the first circumference, it may be done so using the same electrodes that originally sensed the circumferential contraction.

Figure 14:
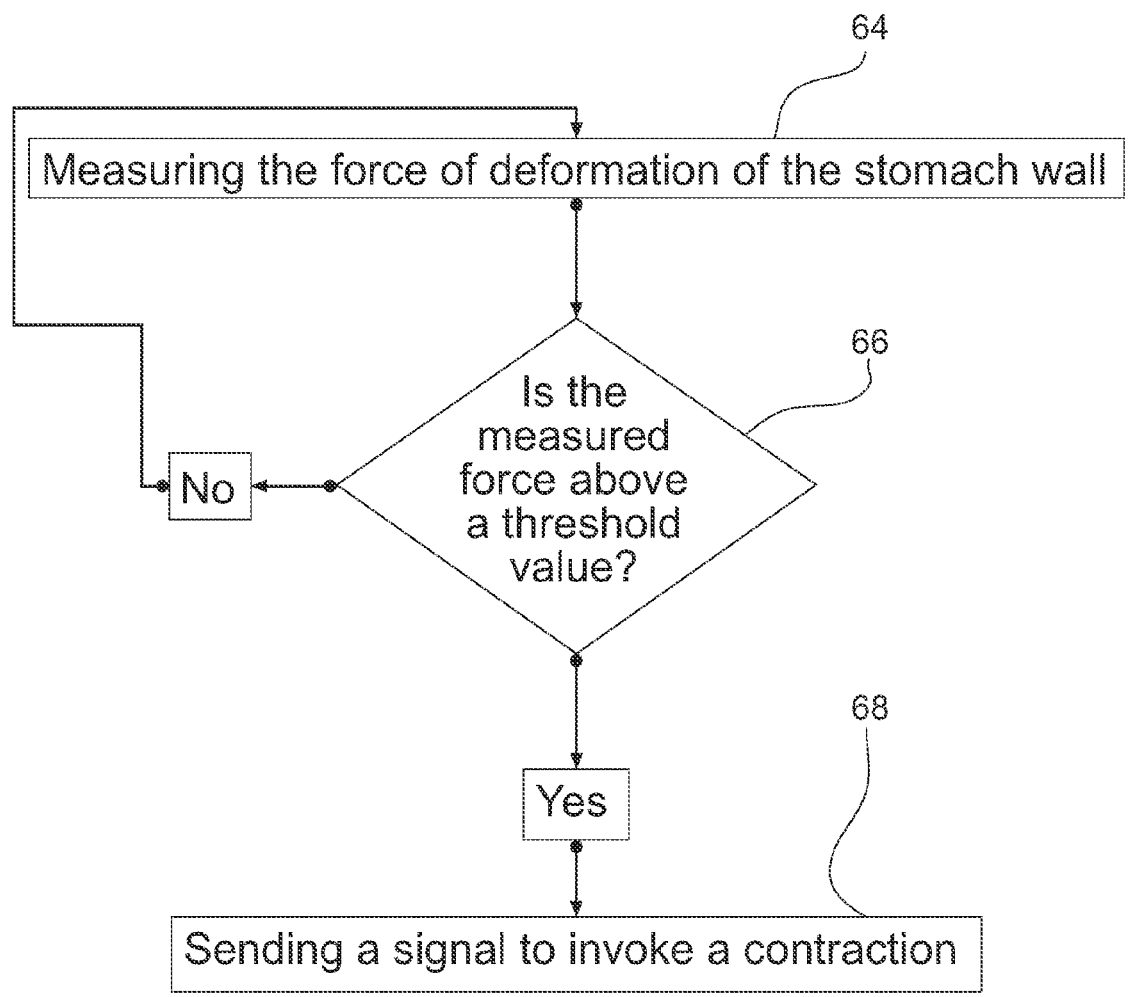
FIG. 14 shows a method of detecting a circumferential contraction using the force of deformation of the stomach wall.

Referring to FIG. 14, a method for sensing a circumferential contraction using the force of deformation of the wall of stomach 18 is illustrated. In step 64, the force of deformation of the wall of stomach 18 is measured. This measuring is done using force transducer 46, or both of force transducers 46 and 48. In step 66, the measured force is compared to a threshold value. Since the force will increase during a circumferential contraction, if the measured force is below the threshold value, than the method returns to step 64 and re-measures the force of deformation. This process is repeated, until a measured force value is returned that is above the threshold value. Referring to FIG. 10B, because force measurements can drift over time, it may be necessary to process the measured force prior to comparing it to the threshold value. This processing may involve subtracting a moving average from the measured force, in order to compensate for drift variations in the measured force. The moving average may be calculated using the past twenty seconds of measured force values. Alternatively, other ranges of time of measured force values may be used to calculate the moving average. Additionally, a different processing method other than subtracting a moving average may be employed, such as higher-end statistical calculations. Referring to FIG. 14, once a circumferential contraction has been sensed, as indicated by a processed measured force value above the threshold value, a signal is sent to invoke a contraction in step 68.

The feedback loop using force transducers 46 and 48 was able to control the NGES timing. Referring to FIGS. 6A and 6B, when a natural circumferential contraction 80 at force transducer 48 reached a stimulation threshold 82, controller 16 was turned on and initiated an NGES at time 83, producing a retrograde circumferential contraction 84 starting at second set of electrodes 30. Before contraction 80 could reach force transducer 46, NGES-invoked retrograde contraction 84 was produced which overrode the propulsive contraction. The magnitudes of electrically-invoked contractions 84 exceeded the magnitudes of natural circumferential contractions 82, as measured by force transducers 46 and 48. If a natural contraction occurred within 40 seconds from the last stimulation, invoked retrograde contraction 84 was lower in amplitude, indicating that a refractory period of 20 seconds was probably not sufficient for repeated stimulation. Referring to FIGS. 7A and 7B the frequency of natural contractions 80 significantly diminished immediately after the first NGES-invoked retrograde contraction 84 was administered, a phenomenon that could be regarded as NGES-invoked gastro paresis.

Figure 12:
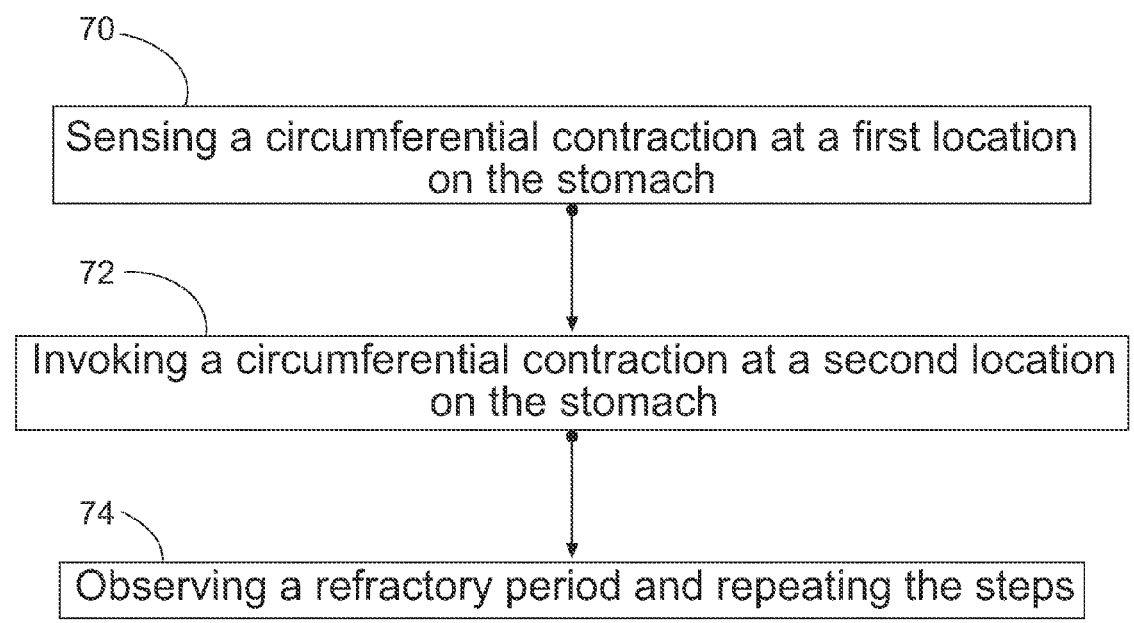
FIG. 12 shows a method of sensing a contraction, invoking a retrograde contraction, and observing a refractory period before repeating.

Referring to FIG. 12, another method of inducing controlled gastro paresis is illustrated. In step 70, a circumferential contraction is sensed at a first location on the stomach, in a similar fashion as that described for step 54 in FIG. 11. In step 72, a circumferential contraction is invoked at a second location in response to the sensed circumferential contraction, in a similar fashion as that described for step 56 in FIG. 11. In step 74, a refractory period is observed after step 72. The refractory period may be longer than twenty seconds, in order to prevent stomach 18 from adapting to the gastric stimulation applied it. Steps 70, 72 and 74 may now be repeated until it is desirable to cease. It may be advantageous to employ the method described in FIG. 12 in addition to the method described above for sensing a circumferential contraction anywhere in the gastrointestinal tract. That way, a retrograde circumferential contraction can be induced to override a natural circumferential contraction at any desirable point in the gastrointestinal tract.

Figure 3A:
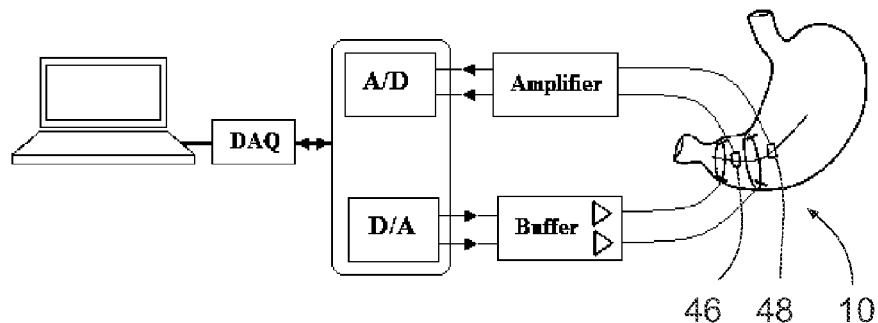
FIG. 3A shows a control diagram of a feedback controlled gastric stimulator that senses circumferential contractions using a force transducer.
Figure 3B:
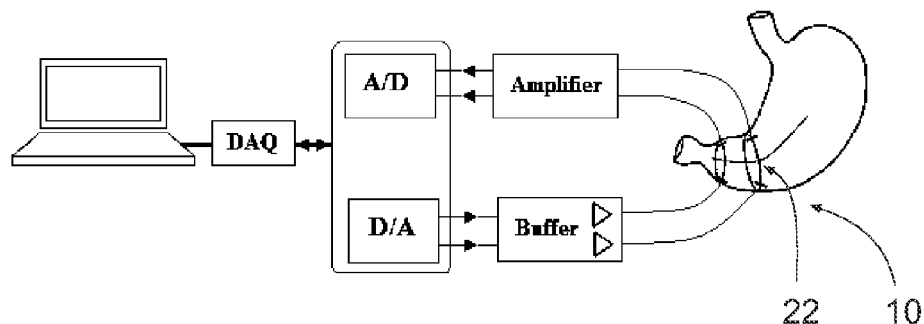
FIG. 3B shows a control diagram of a feedback controlled gastric stimulator that senses circumferential contractions using impedance.

These above measurements (impedance in FIG. 13, force of deformation in FIG. 14) were used to control the NGES using a level-based threshold which signalled controller 16 to produce a retrograde stimulating pattern starting from the distally implanted second set of electrodes 30. The threshold level of the trigger was set at a fixed value and was turned on when the difference between the instantaneous feedback signal and its moving average over the last 20 seconds reached this value. This subtraction of the moving average from the instantaneous feedback signal representing gastric motility was introduced to remove the drift of the feedback variable. After each triggered stimulation sequence a refractory period of 20 seconds was imposed to give the gastric tissue the chance to recover from the NGES. Referring to FIGS. 3A and 3B, block-diagrams of the overall feedback-controlled NGES technique used in the study are illustrated. Referring to FIG. 3A, gastric stimulator 10 employs the use of force transducers 46 and 48 to sense circumferential contractions. Referring to FIG. 3B, gastric stimulator 10 senses circumferential contractions using the impedance measured between electrodes of first set of electrodes 22.

In this document, two different feedback mechanisms, a force-based feedback control and an inter-electrode impedance-based feedback control are utilized to improve the effectiveness of retrograde NGES for the treatment of obesity. Both methods were tested in acute canine experiments and were able to control the timing of controller 16 in a very similar and comparable fashion.

In an implantable gastric stimulator 10, an inter-electrode impedance-based feedback system may be preferred over a force based feedback setup in order to keep the surgical procedures minimally invasive and to reduce the technological requirements to the device. Further, the inter-electrode impedance-based feedback employs the same sets of electrodes 22 and 30 used for stimulation and therefore no extra wires have to be implanted. Only minimal hardware enhancement of an implantable NGES device would be required to practically implement such system.

The invoked gastro paresis observed in this document shows the potential of this apparatus and method to reduce food intake by delaying gastric emptying. The reduced frequency of spontaneously-existing gastric contractions 80 disturbed on demand by the NGES-invoked retrograde contractions 84 are the main factor contributing to delaying gastric emptying which in turn could provoke early satiety and reduced food intake.

A previous chronic animal study of NGES for the treatment of obesity (Aelen P., et al., "Manipulation of Food Intake and Weight Dynamics Using Retrograde Neural Gastric Electrical Stimulation in a Chronic Canine Model, Neurogastroenterology and Motility") showed adaptation of the gastric smooth muscle when stimulated with the same voltage amplitude level over several days. With the feedback loop closed, stimulation would only be applied in the presence of a natural contraction of pre-determined strength, instead of continuously stimulating (and fatiguing) the smooth muscle. These fewer NGES-invoked contractions would probably make it less likely to cause muscle adaptation to the applied voltage stimulation levels. Further, if muscle adaptation still occurs over a longer period of time, the voltage amplitude of stimulation can be adjusted to a higher level by measuring the amplitude of the invoked contractions with the feedback mechanism itself. In addition to the reduced chance of muscle adaptation by this more efficient way of stimulation, the demands on the batteries of the implant would be significantly lower. Another energy saving possibility could be found in the amplitude of stimulation. The amplitudes of the invoked retrograde contractions were higher then these of the Erythromycin-driven contractions, and the voltage amplitude of stimulation could probably be lowered to produce a contraction of similar strength to a natural contraction. This in turn would have a positive effect on the energy demands for implantable gastric stimulator 10, would further reduce the muscle adaptation problem, and would diminish further the refractory time so that the state of invoked gastroparesis could be achieved faster and more efficiently.

Two separate feedback methods explored the controllability of gastric stimulator 10. A force transducer-based feedback method and inter-electrode impedance based feedback method both were both able to measure circumferential gastric contractions and to control the timing of stimulation in order to invoke retrograde contractility leading to temporary gastro paresis during eating. The inter-electrode impedance-based feedback method uses the implanted stimulating electrodes for stimulation, making it a preferred technique to embed in an implantable autonomous neurostimulator.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims. Immaterial modifications may be made to the embodiments described here without departing from what is covered by the claims.

What is claimed is:

1. An apparatus comprising:
   a set of electrodes adapted for implantation at a first portion of gastrointestinal tract, wherein said set of electrodes is configured for both detecting a natural circumferential contraction at the first portion of gastrointestinal tract and for providing electrical stimulation to induce a circumferential contraction to the first portion of gastrointestinal tract; and a controller configured to receive a natural circumferential contraction signal from said set of electrodes, and is further configured to output an electrical signal to the same said set of electrodes to induce a circumferential contraction of the gastrointestinal tract only upon receiving the natural circumferential contraction signal from said set of electrodes.

2. The apparatus of claim 1 further comprising a second set of electrodes for providing a second electrical stimulation to induce a second circumferential contraction, wherein said second set of electrodes is adapted for implantation at a second portion of the gastrointestinal tract that is distal to the first portion of the gastrointestinal tract.

3. The apparatus of claim 2, wherein said controller is configured to induce circumferential contraction to said set of electrodes and said second set of electrodes such that the circumferential contractions generated by said set of electrodes and said second set of electrodes overrides natural contractions of the gastrointestinal tract.

4. The apparatus of claim 3, wherein said controller is configured to induce circumferential contractions to said set of electrodes and said second set of electrodes according to a desired synchronized pattern based on information of natural contractions of the gastrointestinal tract.

5. The apparatus of claim 1, wherein said controller comprises an oscillator that applies an interrogation current to said set of electrodes to measure impedance between electrodes for determining occurrence of circumferential contraction at the first portion of the gastrointestinal tract.

6. The apparatus of claim 5, wherein said oscillator is frequency-adjustable.

7. The apparatus of claim 6, wherein said controller is configured to sweep said oscillator through a range of frequencies greater than 5 kHz.

8. The apparatus of claim 7, wherein said controller is configured to sweep said oscillator to a maximum frequency of 500 kHz or less.

9. A method for inducing controlled gastroparesis in the stomach of a subject, said method comprising:

implanting a set of electrodes to a first portion of a subject's stomach, wherein said set of electrodes are configured both to detect a natural circumferential contraction signal from the first portion of the subject's stomach and to generate a circumferential contraction signal at the first portion of the subject's stomach;

detecting the natural circumferential contraction signal from the first portion of the subject's stomach using said set of electrodes; and providing an electrical signal to said set of electrodes using a controller to induce a circumferential contraction at the first portion of the subject's stomach, wherein said controller is configured to provide the electrical signal to said set of electrodes to induce circumferential contraction only upon after receiving the natural circumferential contraction signal from said set of electrodes.

10. The method of claim 9, wherein said set of electrodes are implanted subserosal.

11. The method of claim 9 further comprising the step of implanting a second set of electrodes for providing a second electrical stimulation to induce a second circumferential contraction, wherein said second set of electrodes are implanted at a second portion of the gastrointestinal tract that is distal to the first portion of the gastrointestinal tract.

12. The method of claim 11, wherein said controller is configured to provide the electrical signal to said set of electrodes and said second set of electrodes such that the circumferential contraction generated by said set of electrodes and said second set of electrodes overrides natural contractions of the gastrointestinal tract.

13. An apparatus comprising:

a first set of electrodes and a second set of electrodes, wherein both of said first set of electrodes and said second set of electrodes are adapted for implantation at a gastrointestinal tract, and wherein both of said first set of electrodes and said second set of electrodes are configured to (i) generate a circumferential contraction signal when the natural circumferential contraction is detected; or (ii) provide electrical stimulation to induce a circumferential contraction; and a controller configured to provide interchangeable utilization of each of said set of electrodes as either a circumferential contraction signal sensor or as a circumferential contraction generator, wherein said controller is further configured to generate a signal to induce circumferential contraction only upon receiving a contraction signal from one of said set of electrodes.

* * * * *